United States Patent [19]

Jamzadeh

[11] Patent Number: 5,488,456
[45] Date of Patent: Jan. 30, 1996

[54] METHOD AND APPARATUS FOR DETECTING WHICH SIDE OF A RECORDING SHEET CONTAINS A COATING

[75] Inventor: Feraydoon S. Jamzadeh, Fairport, N.Y.

[73] Assignee: Eastman Kodak Company, Rochester, N.Y.

[21] Appl. No.: 168,003

[22] Filed: Dec. 15, 1993

[51] Int. Cl.$^6$ ............................ G03G 15/00; G01N 21/64
[52] U.S. Cl. ........................ 355/203; 355/311; 250/559.4
[58] Field of Search .................. 355/203, 205, 355/206, 311, 132; 250/559, 559.4, 559.41; 356/51

[56] References Cited

U.S. PATENT DOCUMENTS

| | | | |
|---|---|---|---|
| 4,591,271 | 5/1986 | Byers | 356/432 |
| 4,825,257 | 4/1989 | Yoshino et al. | 355/132 |
| 5,004,928 | 4/1991 | Suzuki et al. | 250/559 |
| 5,081,484 | 1/1992 | Nakata et al. | 355/27 |
| 5,282,001 | 1/1994 | Watson | 355/208 |

*Primary Examiner*—Joan H. Pendegrass

[57] ABSTRACT

In printers using specially coated receiver, it is important that the coated receiver is loaded in the image-recording apparatus with the coated surface facing in the proper direction. Image stabilizers are used to extend the life of the image and are used to absorb ultraviolet light (UV) from sunlight and prevent the UV light from breaking down and decomposing the thermoplastic coating. Because these stabilizers are coated with the thermoplastic coating, the UV-absorbing materials therein can be used to detect the proper orientation of the recording sheet in the printer. Beams of light are directed against both surfaces of the recording sheet to detect the presence or absence of UV-absorbing material. In another embodiment, UV light fluoresces at a higher wavelength and this presence or absence of the higher wavelength is detected and from the measured light information reflected from each surface, the orientation of the recording sheet can be determined.

5 Claims, 4 Drawing Sheets

5,488,456

METHOD AND APPARATUS FOR DETECTING WHICH SIDE OF A RECORDING SHEET CONTAINS A COATING

BACKGROUND OF THE INVENTION

1. Technical Field of the Invention

The present invention relates generally to image-recording apparatus such as a printer or a copy machine and more particularly, for detecting and evaluating coatings on a receiver sheet, which coatings are difficult to detect and evaluate by visual observation.

2. Background of the Invention

It is extremely important that the receiver (transparency or reflection media like receiver) gets loaded with the correct surface facing the proper direction in an apparatus such as a thermal printer or electrophotographic printer that uses a thermoplastic-coated receiver. If the receiver is fed with the wrong side facing the process, the thermoplastic layer will stick to the surface of the transfer drum and the drum must then be cleaned thoroughly and may even have to be changed.

U.S. Pat. No. 5,081,484, issued to Nakata et al on Jan. 14, 1992 discloses a photographic copier that uses specially coated receiver as a receiver. A photosensitive material is exposed and then put in contact with this receiver under pressure. Exposed photocells or microcapsules, as they are sometimes called, are transferred to the receiver, while unexposed cells remain on the photosensitive material. To insure that the receiver is inserted with the correct side of the specially coated receiver facing the photosensitive material, another coating is made on one end of the receiver and only on one side. This extra coating exhibits a particular electrical resistance. Conductive arms in the path of the receiver will read electrical resistance across the receiver as it passes under these arms. When the special-electrical-resistance coating portion of the receiver passes under these arms, a predetermined amount of conductivity is read. This indicates that the receiver was inserted correctly. However, if the predetermined amount of conductivity is not read, a flag is set indicating incorrect receiver loading or improper receiver type. The extra costs of coating a special-electrical-resistance layer is a significant drawback associated with this invention. Another potential problems exists and that is because the coating of the special-electrical-resistance layer is a separate step in addition to the coating of the photo-layer, and coating the special-electrical-resistance layer on the wrong side or the wrong corner of the receiver is a clear possibility.

Another method of surface detection suggested by U.S. Pat. No. 5,081,484 teaches coating a dedicated non-imaging corner of the receiver with dyes. The dyes of a particular color will be used to make these markings. Because the color of the dye is visible, the correct surface of the receiver can be identified by the operator. Also, the correct surface can be identified by the machine if the optical sensors aimed at the receiver surface are tuned for the particular wavelength, i.e., color, of the visible dye. The major disadvantage of this method is the extra visible color markings that are not part of the printed image. The extra receiver surface area used for these markings cannot be used for imaging and is, therefore, wasted. The fact that an additional manufacturing step must be taken to coat the marks with dye is another disadvantage.

U.S. Pat. No. 4,591,271, issued to Byers on May 27, 1986 shows an apparatus that detects coating-side versus no coating-side of any material (transparent or opaque), by applying a puff of condensable vapor to both sides. The coated side absorbs the vapor and does not condense, while the non-coated surface will condense the vapor and cause some fogging on that side. By shining a light to both sides, one can detect which side contains the special coating. The fog on the non-coated side will absorb most of the incident light and a small amount of light is reflected. The coated side, however, will reflect most of the incident light. The reflected light from both sides are compared to determine the coated side versus the non-coated side. This technique applies only to materials that do not contain any coating on one side. Usually, both sides of the receiver sheets are coated with different coatings. The front is coated with the image-sensitive material and the back is covered with a plain resin coating to extend the receiver life and increase its stability as the humidity changes. Therefore, both sides of a normal imaging-type receiver will absorb the condensable vapor and not fog. This can present a problem when using this technique. Furthermore, the act of blowing vapor onto imaging receivers just before imaging takes place, will increase the chance of depositing dust particles, specks and other residue on the receiver sheet. Accordingly, the dust particles and specks will interfere with the normal imaging process and will result in a defect in the final image.

U.S. Pat. No. 5,004,928, issued to Suzuki et al on Apr. 2, 1991 discloses an ink-jet printing apparatus that detects the reflectance of both sides of the receiver simultaneously. By comparing these two signals, the apparatus detects which side of the receiver can be exposed with ink and whether it is inserted correctly. The shortcoming associated with this technique is that if the reflectance of both sides of the receiver are similar, it will fail to correctly distinguish the receiver side. Receivers used for photographic applications, as well as thermal printer receiver, are coated on both sides and exhibit similar reflectance. Furthermore, this technique will not work well with different finishes on each of the surfaces of the receiver. A matte finish on the top surface of a receiver will show lower reflectance than the rear of the receiver. However, a glossy finish on the top surface of the receiver will show considerably higher reflectance than the rear of the receiver.

SUMMARY OF THE INVENTION

In printers that use a specially coated receiver, it is extremely important that the receiver (paper) is loaded with the correct surface facing in the proper direction. It is an object of the present invention to detect on which side of the receiver sheet the special coating is on. If receiver is fed with the wrong side facing the process, the thermoplastic layer will stick to the transfer drum and the drum must be cleaned thoroughly and may even have to be replaced. The present invention provides a more vigorous method of detecting the wrong side of the receiver. The present technique and circuitry allows the surface properties of the two sides of the receiver to be more similar than in the past and still be able to detect which side of the receiver is to be directed toward the process when loaded. With the present invention, not only the correct surface of the receiver can be identified, but the system can also determine if the inserted receiver is of the wrong type and does not belong to that particular class of printers.

The present invention detects the ultraviolet (UV) absorbing material that is coated along the thermoplastic layer on the imaging side of the receiver. The detection of this material is independent of the surface texture of the receiver, i.e., glossy finish or matte finish. Because the UV-absorbing material is coated simultaneously with the thermoplastic layer, there is no chance that it could be coated on the wrong side of the receiver and it does not require a separate manufacturing step.

The present invention provides a detecting device for use in an image recording apparatus and detecting the orientation of an image-recording sheet having front and rear surfaces that has a coating having an ultraviolet-absorbing thermoplastic material on the front surface. The detecting device comprises means for directing an ultraviolet light against both surfaces of the recording sheet and means for comparing the amount of reflected light from each surface. There are also means for determining which surface absorbed the ultraviolet light and if ultraviolet light was absorbed by the front surface and that surface was properly oriented.

The present invention further provides a detecting device for use in an image-recording apparatus and detecting the orientation of a recording sheet having front and rear surfaces with a coating and having a coating with an ultraviolet-absorbing material on the front surface of the recording sheet. The detecting device comprising means for directing an ultraviolet light against a surface of the recording sheet and means for measuring the amount of ultraviolet light absorbed by the surface of the recording sheet. Also included are means for comparing the measured amount of ultraviolet light absorbed by the surface of the recording sheet with a reference level to determine the amount of ultraviolet light absorbed and when ultraviolet absorption is detected.

The present invention further provides a method of detecting the orientation of an image-recording sheet having front and rear surfaces that has a coating having an ultraviolet-absorbing material with a coating that fluoresces light at a higher wavelength on the front surface of said recording sheet. The method comprises the steps of directing an ultraviolet light against both surfaces of the recording sheet and measuring the amount of light at said higher wavelength from each surface. Next, the amount of light at the higher wavelength from each surface is compared to determine which surface fluoresced light at a higher wavelength and thus determine if the recording sheet is properly oriented by determining if the light at said higher wavelength was emitted from the front surface.

BRIEF DESCRIPTION OF THE DRAWINGS

This and other objects and features of the present invention will become clear from the following description taken in conjunction with preferred embodiments thereof with reference to the accompanying drawings in which:

FIG. 6A is directed to the use of detectors sensitive to UV light; FIG. 6B is directed to detectors sensitive to blue light that is fluoresced by the UV-absorbing material; and FIG. 6C is directed to the use of a detector on the front side that is sensitive to UV light.

DETAILED DESCRIPTION OF THE PREFERRED EMBODIMENT

Figure 1:
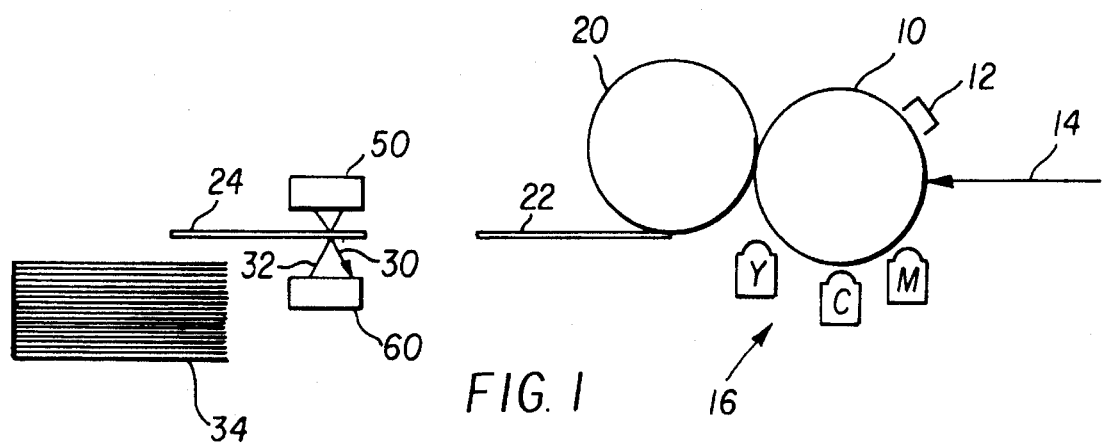
FIG. 1 is a schematic diagram illustrating the overall construction of an electrophotographic printer.

Referring to FIG. 1, the overall construction of an electrophotographic printer is illustrated. The imaging process begins with the charging of the photoconductor drum 10 by the charging unit 12. The charged surface is rotated and passed by the laser beam 14, which exposes the latent image onto the drum. The latent image is developed by one of the color development stations 16. At the same time, the receiver sheet 22 is wrapped around the periphery of the transfer drum 20. The machine's logic and control (LCU) (not shown) will cause the two drums 20 and 10 to engage at the right moment such that the developed image on the photoconductor drum will be transferred to the correct location on the receiver 22. In order to create a color image, this process must be repeated two more times, each time images are developed with different color toner particles.

Photographic quality prints can be produced using this process if very small toner particles are used. The drawback with small particles is the difficulty in transferring them to plain receiver. One solution to this problem is explained in U.S. Pat. No. 4,968,578 where the surface of the receiver sheets is coated with a thermoplastic layer. The receiver is heated before it comes into contact with the toned images on the photoconductive drum. The heat will thaw the receiver surface and make it sticky such that when it comes in contact with the toned images, all the toner particles will adhere to the receiver surface. This results in a very efficient transfer of small toner particles with little residual amounts being left on the photoconductor drum 10. The key to the thermal transfer process just explained is the use of small toner particles in conjunction with the thermoplastic coating layer on the receiver sheets. Referring to FIG. 1, sheets are put in a tray 34 and fed into the machine one at a time. It is very important that the incorrect orientation or wrong side of the sheets are detected before they reach the transfer drum. An error signal is issued and the machine is shut down until an operator can clear the incorrectly loaded receiver. This detection is done by a pair of detectors 50 and 60 in FIG. 1. The detectors inspect a receiver sheet 24 as it is fed from the tray 34. An incident beam 32 is reflected back to the detector as reflected beam 30. If the receiver 24 satisfies the thermoplastic detection test, it is allowed to proceed.

Figure 2:
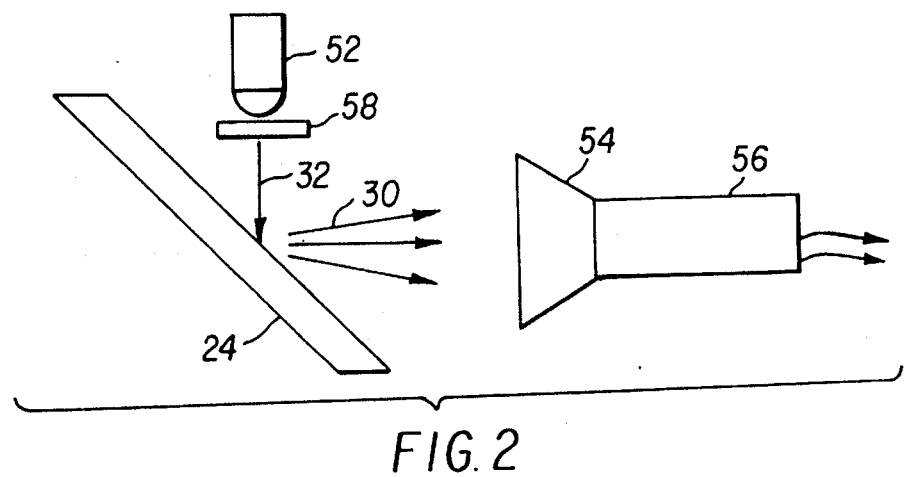
FIG. 2 illustrates the basic construction of the surface-type detectors that are used on both sides of the receiver path.

FIG. 2 illustrates the details of the two surface-type detectors that are used on each side of the receiver path. Each of the detectors is comprised of a light source 52 and a detector 56. The beam from a light source 52 passes through a UV filter 58 for the front surface detector. A filter allows only the UV light to pass through. The incident beam 32 will reflect off the surface of the receiver 24. Depending on how reflective and smooth the receiver surface is, the photocell will receive varying amounts of reflected beam 30. If the receiver surface is rough, the reflected beam 30 will consist of many diverging beams. The light collector cone 54 will absorb the diverging rays. As an alternative to UV filter 58, one may substitute a UV filter that would be located in front of the light collector 54. This particular option may be useful if it is found to be beneficial to use white light as the incident beam 32 instead of the UV light. It should be noted that the more light that reaches the detector 56, the more voltage it will indicate in its output. For example, shiny and glossy receivers will result in a higher voltage out from the detector.

A variation to surface detectors 50 and 60 could be the wavelength that the detector circuitry 56 is sensitive to. These detectors would perform their function if the detector circuitry 56 was tuned for blue light detection. In terms of a wavelength spectrum, the blue region is located at slightly higher wavelengths than the UV rays and adjacent to the UV region. This will be explained further in conjunction with FIGS. 5A and 5B. The operating peak points that these detectors are attempting to detect are in the range between points C and D of FIG. 5B, as explained later.

The rear surface detector 50 may be identical to the front surface detector 60 as was explained earlier. If detectors 50 and 60 are identical, the machine will have the ability to detect if the receiver was inserted correctly or incorrectly as well as detecting whether the receiver is of the correct type. This will be explained in detail below. The rear surface detector 50 could be of a lower cost by not containing any UV filters. This will allow the machine to detect if the receiver was inserted correctly or not. It will not, however, detect if the inserted receiver is of the correct type.

Figure 3:
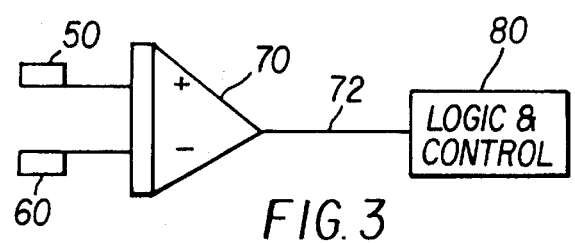
FIG. 3 illustrates how the two surface detectors would be incorporated with the printer's logic and control unit.

FIG. 3 illustrates how the two surface detectors 50 and 60 would be incorporated with the printer's logic and control unit (LCU) 80. The difference between the signals from the two detectors are amplified by amplifier 70. The machine's LCU will interpret the signal to decide if the correct receiver was inserted and if it was inserted with the thermoplastic side up or down.

Figure 5A:
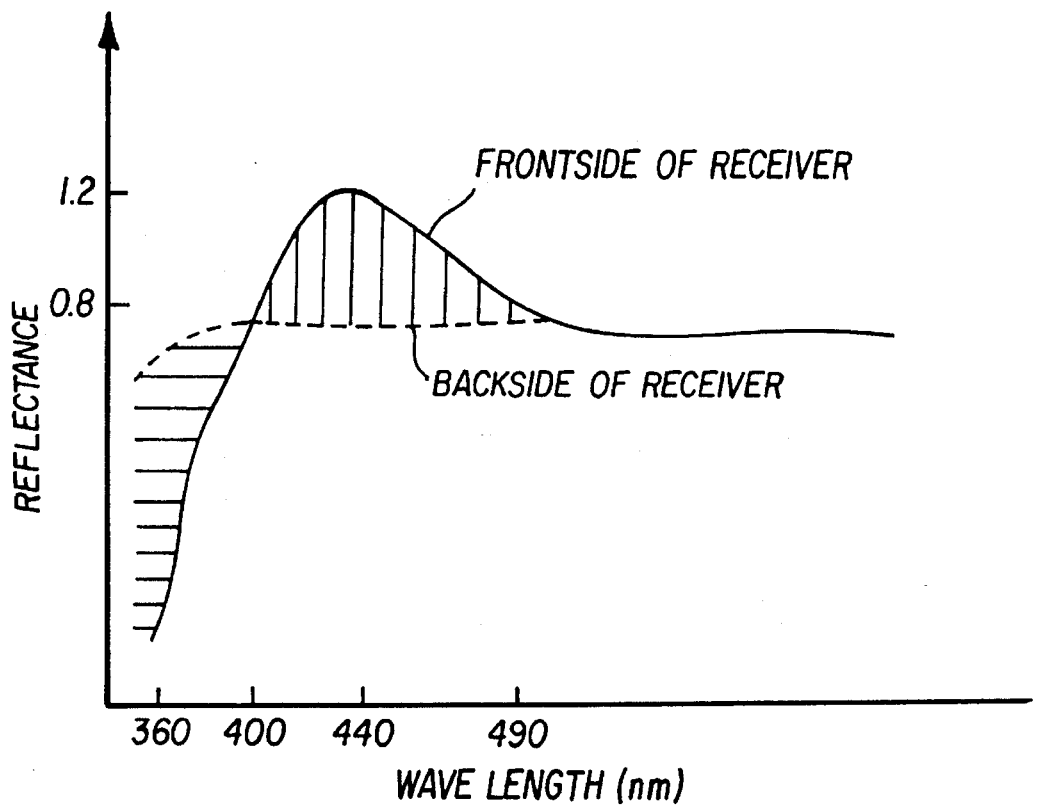
FIGS. 5A and 5B illustrate the spectral responses of the two sides of the receiver with one side exhibiting a peak response at 440 nm.
Figure 5B:
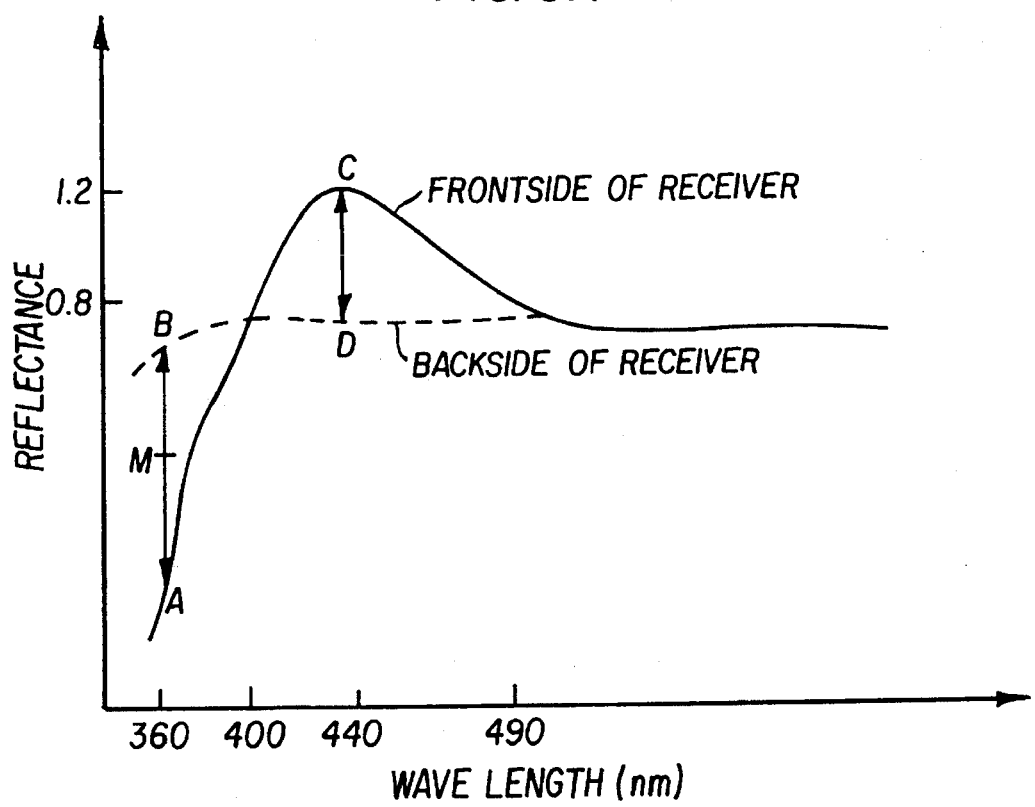

The thermoplastic coated receiver for this invention has different spectral reflectivity on the front and the rear. The spectral response of the two sides of the receiver are shown in FIGS. 5A and 5B. The front side response is shown with a solid line. Notice the sharp decline below 400 nm. (UV region) and the peak response centered at 440 nm. The rear side does not show the sharp decline in the UV region. The reason for the sharp UV absorption is the use of a solid UV stabilizers on or in the thermoplastic. For example, stabilizers sold under the Trademarks Tinuvin® 770 or Tinuvin® 328 by Ciba-Geigy can be used. The UV stabilizers in the preferred embodiment are mixed with the thermoplastic material and coated on the front surface of the receiver sheets. The stabilizers are used to absorb the UV light from the sunlight and are intended to increase the life expectancy of the prints produced if they were left in the sunlight for a long period of time. The UV light from the sun will gradually break down and decompose the thermoplastic coating. Therefore, by incorporating UV absorbent, i.e., UV stabilizers, less UV light will reach the thermoplastic and this will prolong the life of the image impressed thereon. Another benefit associated with use of the UV stabilizer is that it converts the absorbed UV light into visible blue light. It is for this reason that the peak reflectance of the front of the receiver is centered at 440 nm. This phenomenon is referred to as fluorescence. The fluorescent region extends from 400 nm. to 490 nm. as shown in FIGS. 5A and 5B. The fluorescent region is cross-hashed with vertical lines in FIG. 5A. The UV region is cross-hashed with horizontal lines in FIG. 5A. This fluorescing effect is helpful because the thermoplastic will yellow as it gradually breaks down and the combination of blue light and the yellowing of the thermoplastic will combine to render a neutral appearance to the print. As a result, the print will maintain its overall look as time passes and will not appear yellowish as normal photographic prints tend to do with age. The preferred embodiment of the invention requires the tuning of the front detector 60 to look for UV absorption below 400 nm. This way, the system is tuned in to look for certain wavelengths or the absence of that wavelength in the reflectivity signals. The rear detector 50 could also be of the same type as the front detector 60 which is tuned for the UV region with filter 58.

Figure 6A:
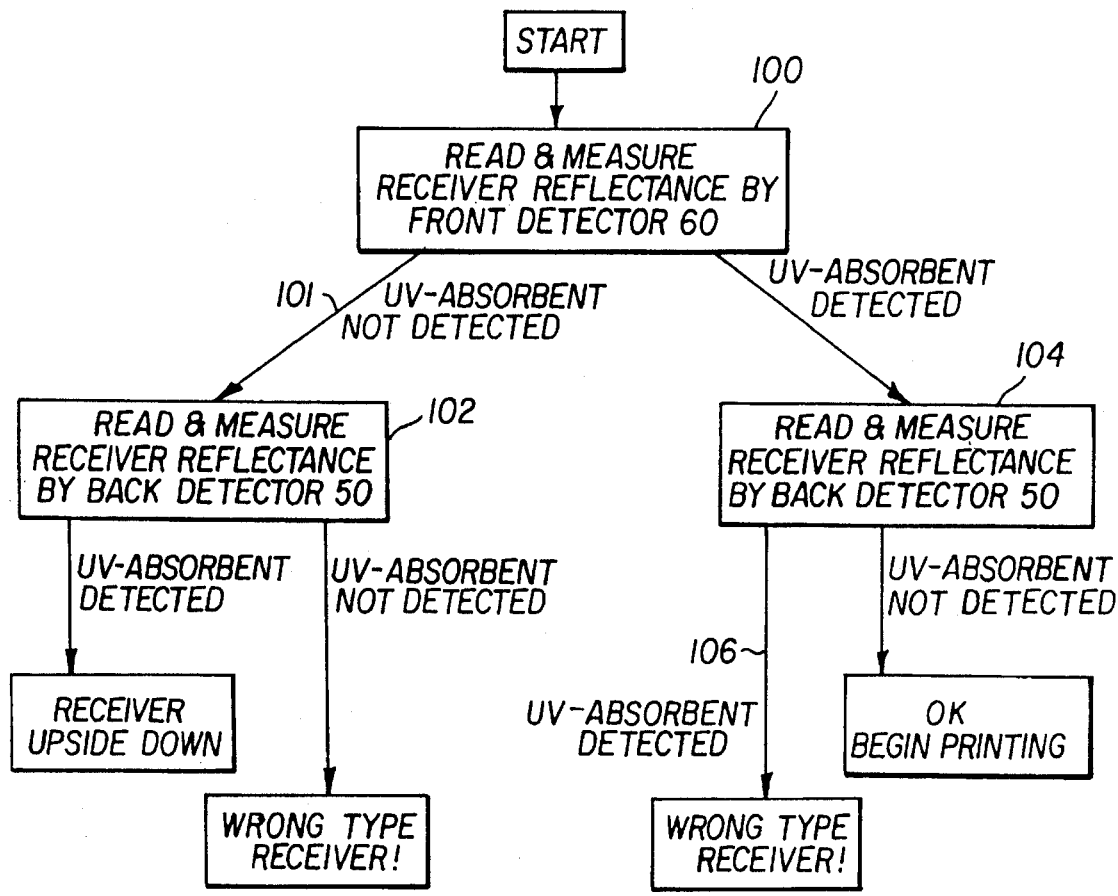
FIGS. 6A–6C illustrate logic flow charts for various embodiments of the present invention.

FIG. 6A is a flow chart explaining the logic steps associated with a preferred embodiment of the present invention. In step 100, it is determined whether the surface of the receiver contains any UV-absorbing material. If it does, in step 104, the rear side of the receiver is examined. If the rear does not contain UV-absorbing material, the correct type of receiver is inserted with the correct side directed toward the respective detectors and printing can commence. In the event the rear signal does indicate UV-absorbing material, the receiver sheet inserted in the machine is of the wrong type. This is because both sides of the receiver sheet contain UV-absorbing material. If, as in step 100, it is determined that the front surface of the receiver does not contain any UV-absorbing material, an error flag is set in step 101. The printing is inhibited even if the machine is in the middle of printing. In an effort to determine what went wrong, step 102 is executed to determine if the rear does not contain UV-absorbing material; if this were the case, the receiver sheet currently inserted in the machine is of the wrong type and the operator will be instructed to remove it. If the rear surface of the sheet contains UV-absorbing material, the receiver sheet is of the correct type, but has been inserted in the machine incorrectly and the operator is warned to remove it and re-orient the receiver sheet correctly. If, in step 100, it is determined that the front side of the receiver sheet contains UV-absorbing material, it is further confirmed that the receiver sheet is of the correct type in step 104. It is possible that some receivers, for some other applications, would require UV-absorbing material on both sides. Step 106 would flag the situation where the wrong type of receivers were inserted into the machine by mistake. At such point, the printing may or may not be allowed to proceed depending on whether the receiver would damage the machine.

Figure 6B:
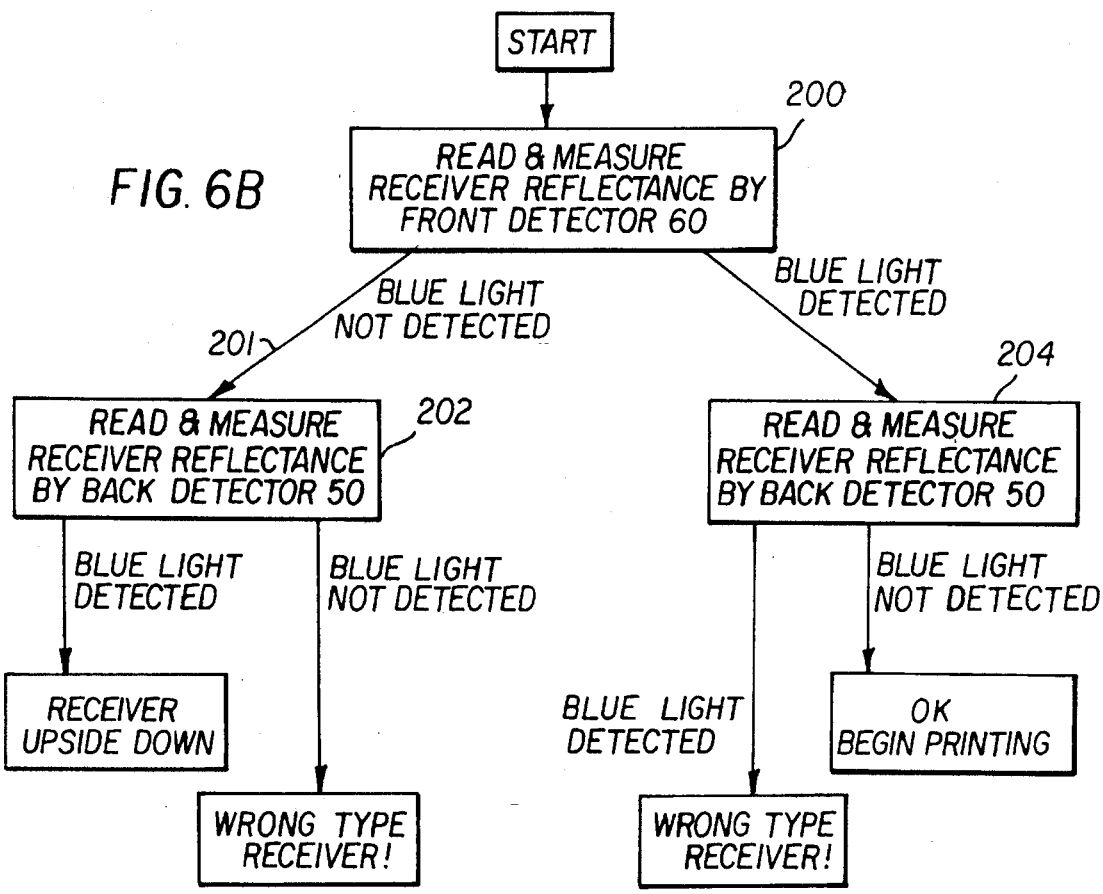

FIG. 6B is a flow chart explaining the logic involved with a second embodiment of this invention where blue light sensitive detectors are used. In step 200, it is determined whether the surface of the receiver sheet is coated with any UV-absorbing material by checking the presence or absence of the fluoresced blue light. If it does fluoresce blue, step 204 examines the rear side of the receiver sheet. If the rear surface does not have a coating containing UV-absorbing material, i.e., no fluoresced blue light is detected, it is assumed that the correct type of receiver is in position with the proper side directed toward the detectors. The printing operation would, of course, be allowed to proceed. If the rear surface contains a UV-absorbing coating, the receiver sheet inserted in the machine is the wrong type because both sides of the receiver contain UV-absorbing material. If, in step 200, it is determined that the front surface of the receiver sheet does not have a coating of UV-absorbing material, an error flag is set in step 201. Printing is not allowed to begin and if the machine were in the middle of printing, it is stopped. To determine what went wrong, step 202 is executed. If the rear surface of the receiver does not have a coating of UV-absorbing material either, i.e., by not detecting any fluoresced blue light, then the receiver sheet inserted in the machine is the wrong type and the operator will be instructed to remove it. If the rear surface of the receiver does have a coating of UV-absorbing material, which is detected by fluoresced blue light, then the receiver sheet is the correct type but it has been inserted in the machine upside down. The operator is instructed to remove it and insert it in the correct way.

It should be understood that it is intended that in the present scope of this invention, one may add infrared absorbing material to the receiver's front and rear surfaces and program the respective detectors to respond accordingly. However, the advantage associated with the preferred embodiment is the fact that the UV-absorbing material is used to increase the life expectancy of the prints and maintains their appearance over time. The preferred embodiment of the present invention is seen to have taken advantage of the existence of the additive to the plastic coating to provide a means for detecting the correct side of the receiver when inserted into the apparatus.

Figure 4:
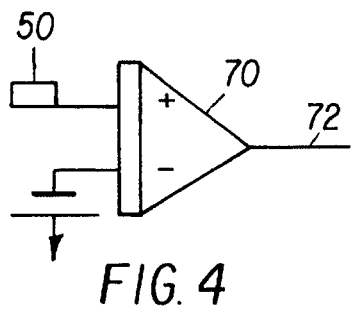
FIG. 4 illustrates another embodiment in which only a single detector is used to look for the UV absorbent material or lack of it.

It should be understood that using two detectors results in a doubling of the signal-to-noise ratio in the detection process. This is achieved by looking for UV absorption on the front and the lack of UV absorption on the rear surface of the receiver sheet. The front detector will output low or no voltage and the rear detector would give a high voltage output. In FIG. 5B, points A and B correspond to the responses of the front detector 60 and rear detector 50, respectively. The dynamic range, i.e., the tolerance for errors because of drifts and noise, that the system can operate within is shown by the A–B magnitude. By sending these two signals to a differential amplifier as shown in FIG. 3, one obtains a strong positive voltage when the receiver is inserted correctly and a negative voltage is detected when the receiver is inserted upside down and incorrectly. It is possible to use a single detector to look for the UV absorbent or lack of it from only one side. This will require that there be a comparison with the output voltage of the detector against a fixed or experimentally defined reference voltage. FIG. 4 shows this embodiment and it is clear that the device is less reliable in the presence of noisy or weak signals since it has a lower signal of noise ratio. In FIG. 5B, the mid-point M corresponds to such a fixed reference voltage. It is clear the dynamic range, i.e., the tolerance for errors because of drifts and noise, is reduced to the B–M or A–M magnitude. When the rear surface of the receiver is examined, the detector 60 will sense point B. When the front surface of the receiver is examined, the detector 60 will sense point A. The manufacturing variability of receivers or the buildup of dirt and dust on detector 60 may reduce the dynamic range by moving points A and B towards each other. Obviously, the embodiment shown in FIG. 3 will perform better because the entire dynamic range of A–B is used and not B–M or A–M. Such an apparatus would allow for the continued and reliable operation of the device even in less than ideal and demanding conditions. Examples of these conditions could be in a very dusty and unclean environment or when the machine has not been cleaned during its normal service intervals. Thus, it can be seen that the apparatus shown in FIG. 3 can detect the incorrect type of the receiver more reliably than the apparatus illustrated in FIG. 4.

Figure 6C:
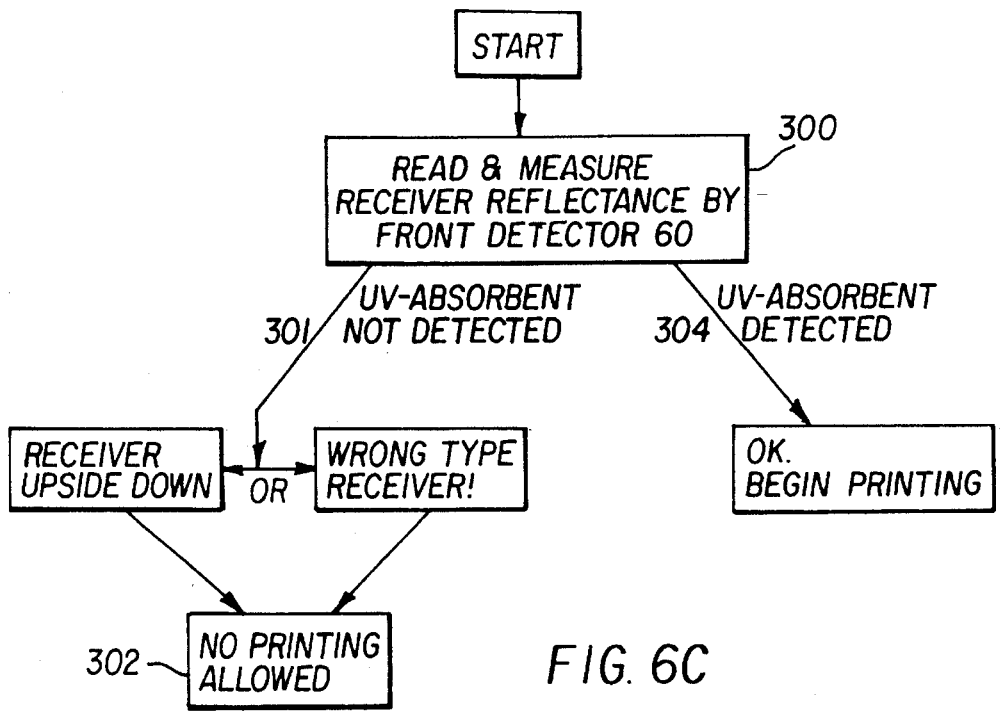

FIG. 6C is a flow chart explaining the logic behind the third embodiment of the present invention where a single UV sensitive detector is used. In step 300, it is determined whether the surface of receiver contains any UV-absorbing material. If it does, in step 304 the printing is allowed to proceed. If, in step 300, it is determined that the front surface of the receiver sheet does not contain any UV-absorbing material, an error flag is set in step 301. Printing is inhibited and if the machine was printing, it is stopped. Because we cannot determine what went wrong, two possibilities exist. Either the rear surface of the receiver is not coated with any UV-absorbing material and the receiver sheet inserted in the machine is the wrong type or the rear surface of the receiver is coated with a UV-absorbing material and the receiver is the correct type, but it has been placed in the machine upside down. Either way, the operator is instructed to remove the receiver in step 302.

While the invention has been described in conjunction with specific embodiments thereof, it is evident that many alternatives, modifications and variations will be apparent to those skilled in the an in light of the foregoing description. Accordingly, it is intended to embrace all such alternatives, modifications and variations as fall within the spirit and broad scope of the appended claims.

I claim:

1. A detecting device for an image-recording sheet having front and rear surfaces that have coatings having an ultraviolet-absorbing material that fluoresces light at a higher wavelength on the front surface, said detecting device comprising:

means for directing an ultraviolet light against both surfaces of the recording sheet;

means for measuring the amount of light at said higher wavelength from each surface;

means for comparing the amount of light at said higher wavelength from each surface to determine which surface fluoresced light at a higher wavelength; and means for determining if the recording sheet is properly oriented by determining if the light at said higher wavelength was emitted from the front surface.

2. A detecting device as set forth in claim 1 wherein the means for comparing finds the presence of fluoresced light at said higher wavelength by both the front surface as well as the rear surface, indicating the use of the wrong type of image-recording sheet.

3. A detecting device as set forth in claim 1 wherein the means for comparing finds the presence of fluoresced light at said higher wavelength by neither the front surface nor the rear surface, indicating the use of the wrong type of image-recording sheet.

4. A method of detecting the orientation of an image-recording sheet having front and rear surfaces, only the front surface of which has a coating having an ultraviolet-absorbing material that fluoresces light at a higher wavelength, said method comprising the steps of:

directing ultraviolet light against both surfaces of the recording sheet;

measuring the amount of light at said higher wavelength from each surface;

comparing the amount of light at said higher wavelength from each surface to determine which surface fluoresced light at a higher wavelength; and determining if the recording sheet is properly oriented according to which surface emitted the light at said higher wavelength.

5. A method of detecting the orientation of a recording sheet having front and rear surfaces, the front surface of which has a thermoplastic coating and an ultraviolet absorbing material coated on the thermoplastic coating to protect the thermoplastic coating from aging, said method comprising the steps of:
- directing ultraviolet light against both surfaces of the recording sheet;
- detecting the amount of light reflected from each surface;
- comparing the amount of light reflected from the surfaces of the recording sheet to determine which surface absorbed the most ultraviolet light; and
- determining the correct orientation of the recording sheet according to the determination of the surface that absorbed the most ultraviolet light.

* * * * *